(12) United States Patent
Kawabata et al.

(10) Patent No.: US 10,952,631 B2
(45) Date of Patent: Mar. 23, 2021

(54) BIOMAGNETISM MEASUREMENT DEVICE

(71) Applicants: National University Corporation Tokyo Medical and Dental University, Tokyo (JP); TDK CORPORATION, Tokyo (JP)

(72) Inventors: Shigenori Kawabata, Tokyo (JP); Satoshi Sumiya, Tokyo (JP); Shuichi Okawa, Tokyo (JP)

(73) Assignees: National University Corporation Tokyo Medical and Dental University, Tokyo (JP); TDK CORPORATION, Tokyo (JP)

( * ) Notice: Subject to any disclaimer, the term of this patent is extended or adjusted under 35 U.S.C. 154(b) by 699 days.

(21) Appl. No.: 15/501,777

(22) PCT Filed: Aug. 5, 2015

(86) PCT No.: PCT/JP2015/072217
§ 371 (c)(1),
(2) Date: Feb. 3, 2017

(87) PCT Pub. No.: WO2016/021633
PCT Pub. Date: Feb. 11, 2016

(65) Prior Publication Data
US 2017/0238834 A1     Aug. 24, 2017

(30) Foreign Application Priority Data
Aug. 5, 2014    (JP) .................................. 2014-159424

(51) Int. Cl.
*A61B 5/05*     (2006.01)
*A61B 5/04*     (2006.01)
(Continued)

(52) U.S. Cl.
CPC ............ *A61B 5/05* (2013.01); *A61B 5/04005* (2013.01); *A61B 5/04007* (2013.01);
(Continued)

(58) Field of Classification Search
CPC ....... A61B 5/05; A61B 5/6885; A61B 5/6876; A61B 5/407; A61B 5/062; A61B 5/04005
(Continued)

(56) References Cited

U.S. PATENT DOCUMENTS

| 5,379,765 A | 1/1995 | Kajiwara et al. |
| 5,840,024 A | 11/1998 | Taniguchi et al. |

(Continued)

FOREIGN PATENT DOCUMENTS

| JP | H01-151438 A | 6/1989 |
| JP | H01-285246 A | 11/1989 |

(Continued)

OTHER PUBLICATIONS

Extended European Search Report issued in the counterpart European Patent Application.: 15829673.1, dated Jun. 11, 2018 (13 Pages).

(Continued)

*Primary Examiner* — Amanda K Hulbert
*Assistant Examiner* — Philip C Edwards
(74) *Attorney, Agent, or Firm* — Osha Bergman Watanabe & Burton LLP

(57) ABSTRACT

A biomagnetism measurement device includes a tubular body, an inflatable portion inflatable upon supply of gas, and a magnetic sensor portion that detects a magnetic field from outside the tubular body. The inflatable portion is located at a required region of the tubular body, and the magnetic sensor portion is fixed to an inner wall of the inflatable portion. The tubular body and the inflatable portion include (Continued)

the same material, and the wall thickness of the inflatable portion is thinner than that of the tubular body.

6 Claims, 14 Drawing Sheets

(51) Int. Cl.
A61B 5/00 (2006.01)
A61B 5/06 (2006.01)
A61B 5/0515 (2021.01)

(52) U.S. Cl.
CPC ........ A61B 5/04009 (2013.01); A61B 5/0515 (2013.01); A61B 5/062 (2013.01); A61B 5/407 (2013.01); A61B 5/4064 (2013.01); A61B 5/687 (2013.01); A61B 5/6853 (2013.01); A61B 5/6852 (2013.01); A61B 5/6868 (2013.01); A61B 5/6873 (2013.01); A61B 5/6876 (2013.01); A61B 5/6885 (2013.01); A61B 2562/043 (2013.01)

(58) Field of Classification Search
USPC ........................................................ 600/409
See application file for complete search history.

(56) References Cited

U.S. PATENT DOCUMENTS

| 5,910,129 | A | 6/1999 | Koblish et al. |
| 6,266,548 | B1 | 7/2001 | Lamade et al. |
| 7,204,796 | B1* | 4/2007 | Seiler ............... A61B 5/06 600/3 |
| 7,749,215 | B1 | 7/2010 | Ben-Haim et al. |
| 2001/0047133 | A1 | 11/2001 | Gilboa et al. |
| 2002/0050819 | A1* | 5/2002 | Minkoff ......... G01R 33/34046 324/318 |
| 2003/0113303 | A1 | 6/2003 | Schwartz |
| 2004/0102733 | A1 | 5/2004 | Naimark et al. |
| 2004/0111101 | A1* | 6/2004 | Chin ................... A61N 1/0587 606/151 |
| 2006/0287595 | A1* | 12/2006 | Maschke ............... A61B 1/042 600/424 |
| 2007/0222433 | A1 | 9/2007 | Tiernan et al. |
| 2009/0322323 | A1 | 12/2009 | Brazdeikis et al. |
| 2010/0152747 | A1 | 6/2010 | Padiy et al. |
| 2011/0105988 | A1 | 5/2011 | Yeung et al. |
| 2013/0317339 | A1 | 11/2013 | Waldstreicher et al. |

FOREIGN PATENT DOCUMENTS

| JP | H06-38937 A | 2/1994 |
| JP | H09-507128 A | 7/1997 |
| JP | 2000-501977 A | 2/2000 |
| JP | 2001-087392 A | 4/2001 |
| JP | 2002-501769 A | 1/2002 |
| JP | 2003-275164 A | 9/2003 |
| JP | 2004-187717 A | 7/2004 |
| JP | 2005-128035 A | 5/2005 |
| JP | 2006-507082 A | 3/2006 |
| JP | 2006-304851 A | 11/2006 |
| JP | 2011-517575 A | 6/2011 |
| JP | 2013-244408 A | 12/2013 |
| WO | 94/28792 A1 | 12/1994 |

OTHER PUBLICATIONS

The partial supplementary European Search Report issued in corresponding European Application No. 15829673.1, dated Feb. 19, 2018 (14 pages).
International Search Report issued PCT/JP2015/072217, dated Oct. 27, 2015 (5 pages).
Written Opinion of the International Searching Authority issued in PCT/JP2015/072217, dated Oct. 27, 2015 (8 pages).
Notice of Reasons for Refusal issued in Japanese Application No. 2016-540260, dated Sep. 3, 2019 (4 pages).
Notice of Reasons for Refusal issued in Japanese Application No. 2016-540260, dated Mar. 10, 2020 (2 pages).

* cited by examiner

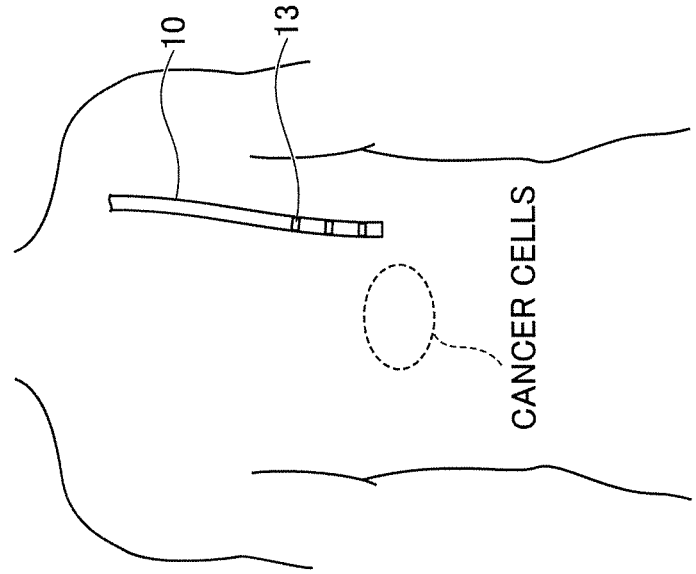
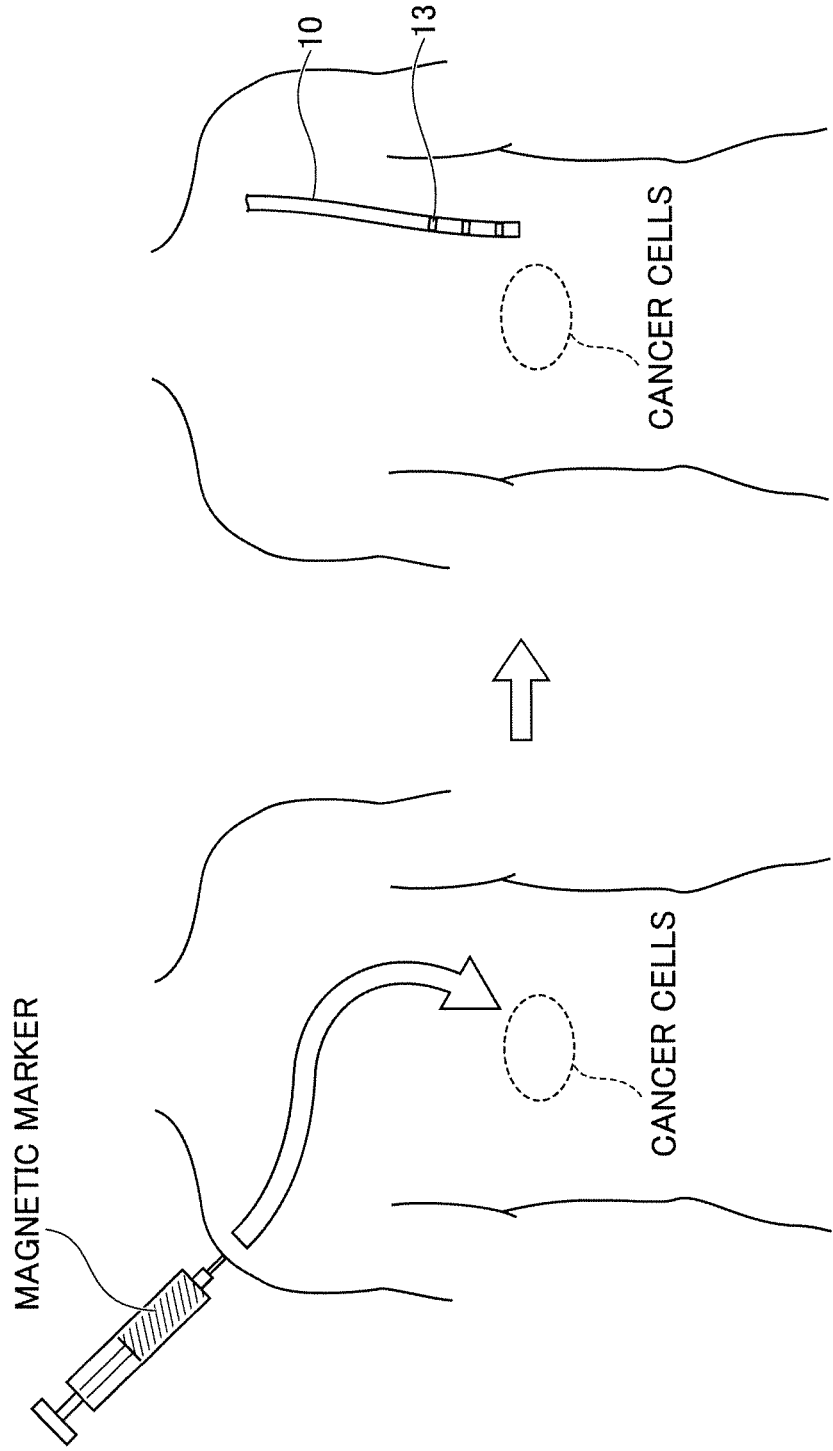

FIG. 8A
FIG. 8B
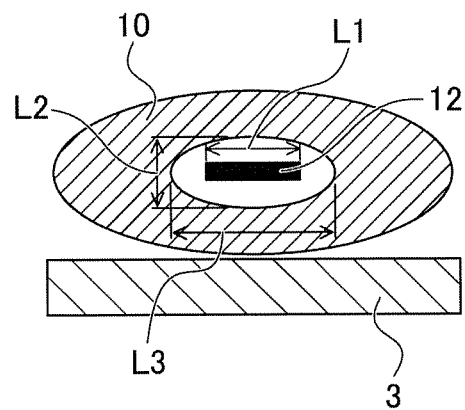
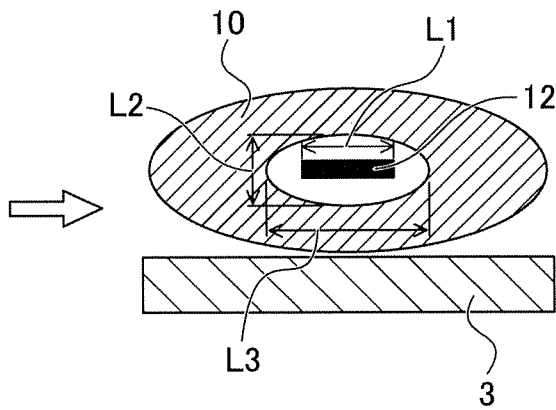

BIOMAGNETISM MEASUREMENT DEVICE

TECHNICAL FIELD

The present invention relates to a biomagnetism measurement device.

BACKGROUND ART

Recent advances in diagnostic imaging systems including those used in the magnetic resonance imaging method (MRI) enables image-based diagnosis of compressive lesions in the spine and disordered areas in the peripheral nerve. However, some of the cases in which compressed areas are clearly indicated on images are actually asymptomatic. For this and other reasons, reliable diagnosis of dysfunctional areas in the spine/peripheral nerve is difficult when image-based morphological information alone is used. Therefore, the neurofunctional diagnosis method using an electrophysiologic approach is still an indispensable method of examination.

As an approach for accurately diagnosing a disordered area, known is measurement of the nerve evoked potential by the inching technique. However, accurate evaluation of a nerve function through the body surface is difficult because the electric current may strongly be affected by the surrounding tissues at a nerve deeply distant from the body surface, in particular at the spine.

Therefore, methods of measuring a spine evoked potential have been proposed in which an electrode is placed in the vicinity of the spine during an operation, or a catheter electrode is transdermally inserted into the epidural space or the subarachnoid space before an operation. However, these methods may impose a tremendous burden on patients, and may also damage the spine upon performing puncture. For these reasons, they are hardly convenient methods of examination to obtain a diagnosis, and thus a simpler electrophysiological approach is desired.

As a simple electrophysiological approach, a biomagnetism measurement system has been proposed, including: a bed 101 on which a subject lies on the back; and a biomagnetism measuring device for measuring a biomagnetism from a measurement target area in the subject from outside the body of the subject, in which the biomagnetism measuring device has a superconducting quantum interference device (SQUID) fluxmeter, and electrically stimulates a nerve tissue of the subject at a high frequency (for example, see Patent Document 1). This biomagnetism measurement system 102 can measure a biomagnetism from a measurement target area without inserting a catheter electrode and the like.

Further, a method has been proposed in which a SQUID fluxmeter contained in the front end of a catheter is allowed to approach a deep area in the body cavity to measure magnetism (for example, see Patent Document 2). According to the approach described in Patent Document 2, magnetism can be measured at a location much closer to the spine, leading to even more improved detection accuracy for a disordered area.

Patent Document 1: Japanese Unexamined Patent Application, Publication No. 2006-304851
Patent Document 2: Japanese Unexamined Patent Application, Publication No. H01-151438

DISCLOSURE OF THE INVENTION

Problems to be Solved by the Invention

However, the approach described in Patent Document 1, in which a biomagnetism at a measurement target area is measured from outside the body of a subject, can only measure an extremely weak biomagnetism as low as about $10^{-14}$ tesla. This may limit the measurement precision. Accordingly, a system capable of performing a measurement with a higher precision has been desired.

Further, even though Patent Document 2 discloses an approach in which a SQUID fluxmeter is contained in the front end of a catheter, there is neither disclosure nor suggestion about how the SQUID fluxmeter is contained, leaving a possibility that magnetism may not accurately be measured due to possible twisting of the SQUID fluxmeter as the catheter is being inserted into the body cavity. Therefore, the device needs to be further improved.

The present invention is made in order to solve the above problems. An object of the present invention is to provide a biomagnetism measurement device capable of accurately diagnosing a disordered area, which can be used simply and conveniently.

Means for Solving the Problems

The present inventors have conducted extensive studies to solve the above problems. As a result, the present inventors find that the above problems can be solved by selecting the shape or position of a magnetic sensor portion, using a predefined sensor, and the like. Then, the present invention has been completed. Specifically, the present invention can provide the followings.

(1) The present invention can provide a biomagnetism measurement device, including: a tubular body; an inflatable portion inflatable upon supply of gas, the inflatable portion being located at a required region of the tubular body; and a magnetic sensor portion for detecting a magnetic field from outside the tubular body, the magnetic sensor portion being fixed to an inner wall of the inflatable portion.

(2) Further, the present invention can provides the biomagnetism measurement device according to (1), in which the tubular body and the inflatable portion are made of the same material, and the wall thickness of the inflatable portion is thinner than that of the tubular body.

(3) The present invention can provide a biomagnetism measurement device, including: a tubular body having approximately elliptic inner shapes in tube cross-sections; at least one magnetic sensor portion for detecting a magnetic field from outside the tubular body; and a connection portion extending within a tube of the tubular body in the approximately same direction as the longitudinal direction of the tubular body, and having the at least one magnetic sensor portion attached at a desired position, in which the length of an inner short side of at least one cross section among the tube cross-sections is shorter than the length of the connection portion in the direction of an inner long side of the same cross section as the at least one cross section, and the length of the inner long side of the at least one cross section is longer than the length of the connection portion in the direction of the inner long side of the same cross section.

(4) Further, the present invention can provide the biomagnetism measurement device according to (3), further including at least one inflatable portion inflatable upon supply of gas, the at least one inflatable portion being located at a required region of the tubular body, in which the at least one magnetic sensor portion includes multiple magnetic sensor portions, and the at least one inflatable portion includes multiple inflatable portions, and the multiple magnetic sensor portions are individually accommodated in the inside of each of the multiple inflatable portions.

(5) Further, the present invention can provide the biomagnetism measurement device according to any one of (1) to (4), in which the magnetic sensor portion is configured to detect a magnetic field along an approximately constant direction in the anatomical position.

(6) Moreover, the present invention can provide a biomagnetism measurement device, including: a tubular body; and at least one magnetic sensor portion for detecting a magnetic field along an approximately superior-inferior direction in the anatomical position, the at least one magnetic sensor portion being provided at a desired position inside the tube of the tubular body.

(7) Further, the present invention can provide the biomagnetism measurement device according to any one of (1) to (4), wherein the at least one magnetic sensor portion includes multiple magnetic sensor portions, and at least one of the multiple magnetic sensor portions includes a triaxial magnetic sensor for detecting magnetic fields along three mutually orthogonal axes, or includes multiple magnetic sensors closely arranged and capable of detecting magnetic fields along three mutually orthogonal axes, and the rest of the multiple magnetic sensor portions each include a uniaxial magnetic sensor for detecting a magnetic field along one predetermined axis among the three axes.

(8) Further, the present invention can provide a biomagnetism measurement device, including: a tubular body; and at least one or more magnetic sensor portions provided at desired positions of the tubular body, in which each of the at least one or more magnetic sensor portions includes a triaxial magnetic sensor for detecting magnetic fields along three mutually orthogonal axes, or includes multiple magnetic sensors closely arranged and capable of detecting magnetic fields along three mutually orthogonal axes.

(9) Further, the present invention can provide the biomagnetism measurement device according to any one of (1) to (8), in which the outer long side of a tube cross-section of the tubular body is 5 mm or less, and the magnetic sensor portion has a magnetic impedance element and/or a magnetic resistance element.

Effects of the Invention

The present invention can provide a biomagnetism measurement device capable of accurately diagnosing a disordered area, which can be used simply and conveniently. Further, the present invention can provide a biomagnetism measurement device which can be used for detecting an affected area using magnetic markers. The conventional pathological examinations for identifying an affected area requires a procedure of tissue examination under a microscope, which is time consuming and troublesome. According to the present invention, such a procedure can be avoided by virtue of the combined use of magnetic markers and the biomagnetism measurement device according to the present invention as described above, enabling rapid and simple identification of an affected area.

BRIEF DESCRIPTION OF THE DRAWINGS

FIG. 6 shows an example of a procedure for detecting an affected area using magnetic markers and the biomagnetism measurement device according to the present invention.

FIG. 8 shows a cross sectional view of the tubular body 10 of the biomagnetism measurement device 1A at the A-A' plane in FIG. 7.

PREFERRED MODE FOR CARRYING OUT THE INVENTION

Below, specific embodiments 1 to 5 of the present invention will be described in more detail, but the present invention shall not be limited in any way to these embodiments. Appropriate modifications can be made to the present invention within the scope of the purposes of the present invention. Note that descriptions may appropriately be omitted for the repeatedly appearing parts, but this shall not limit the spirit of the present invention.

Embodiment 1

Below, the embodiment 1 will be described in detail with reference to FIGS. 1 to 4.

Figure 1:
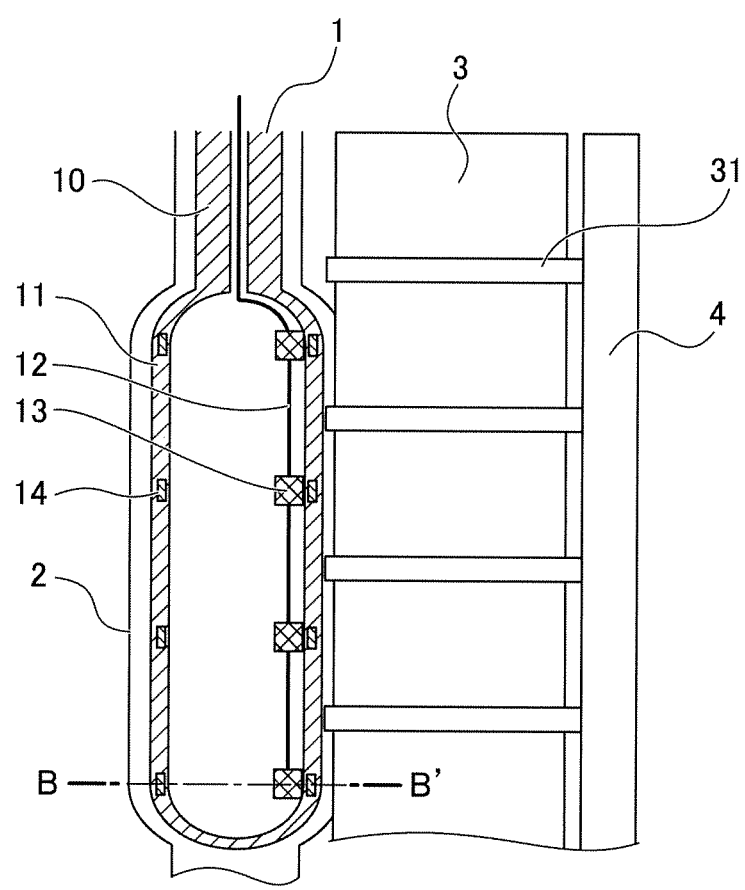
FIG. 1 shows a schematic cross sectional view of a biomagnetism measurement device 1 according to the embodiment 1 of the present invention, and also shows schematically an aspect of use thereof.

FIG. 1 shows a schematic cross sectional view of the biomagnetism measurement device 1 according to the embodiment 1, and also shows schematically an aspect of use thereof. As shown in FIG. 1, the biomagnetism measurement device 1 according to the embodiment 1 includes a tubular body 10; an inflatable portion 11 inflatable upon supply of gas, the inflatable portion 11 being located at a desired region of the tubular body 10; and a magnetic sensor portion 13 for detecting magnetic field from outside the tubular body 10, the magnetic sensor portion 13 being fixed to an inner wall of the inflatable portion 11. Below, each of the components of the biomagnetism measurement device 1 according to the embodiment 1 will be described. Note that the term "biomagnetism measurement device" as used herein means not only a device for measuring a magnetism originated from an organ in the living body (for example, a spine 4 and the like) but also a device for measuring a magnetism originated from a foreign magnetic object introduced into the living body (for example, magnetic markers and the like).

Tubular Body 10

As shown in FIG. 1, the tubular body 10 is a tubular member having a cavity portion inside, and the magnetic sensor portion 13 and a connection portion 12 described below are located in the cavity portion. The biomagnetism measurement device 1 with the magnetic sensor portion 13 accommodated in the cavity portion of the tubular body 10 is to be inserted into a desired position in the body to detect a magnetic field. This can allow for a simple and convenient measurement of magnetism.

In the biomagnetism measurement device 1 according to the embodiment 1, the inflatable portion 11 is positioned in a desired region of the tubular body 10. There is no particularly limitation for the "desired region of the tubular body 10" in the biomagnetism measurement device 1 according to the embodiment 1 as long as the effects of the present invention can be obtained, but it may be, for example, a region in the end side of the tubular body 10 as shown in FIG. 1, or alternatively it may be a region other than the end of the tubular body 10. In particular, the "desired region of the tubular body 10" is preferably a region in the end side of the tubular body 10 as shown in FIG. 1, considering that the length of a portion of the tubular body 10 to be inserted into the body can be minimized.

There is no particularly limitation for the length of the outer long side of a tube cross-section of the tubular body 10, but it is preferably shorter, and more specifically it is preferably 5 mm or less, more preferably 4 mm or less, and even more preferably 3 mm or less so that the tubular body 10 can pass through a fine tube in the human body (for example, a blood vessel, the esophagus, the gastrointestinal tract, and the like) with a less risk of damaging the spine 4, and magnetism can be measured more conveniently. Further, there is no particularly limitation for the cross sectional shapes (inner shape, outer shape) of the tubular body 10, but they may be elliptic or circular. However, the outer shape of a cross section is preferred to be approximately elliptic because the tube itself will be resistant to twisting within the esophagus 2.

Inflatable Portion 11

The inflatable portion 11 is a member which can be inflated by supply of gas, and positioned in a desired region of the tubular body 10. Further, in the biomagnetism measurement device 1 according to the embodiment 1, the magnetic sensor portion 13 is fixed to the inner wall of the inflatable portion 11. In the biomagnetism measurement device 1 according to the embodiment 1, twisting of the magnetic sensor portion 13 within the tubular body 10 can be prevented because the magnetic sensor portion 13 is fixed to the inner wall of the inflatable portion 11. This enables accurate diagnosis of a disordered area.

There is no particular limitation for the materials and the wall thicknesses of the tubular body 10 and the inflatable portion 11, but the tubular body 10 and the inflatable portion 11 are preferably made of the same material, and the wall thickness of the inflatable portion 11 is preferably thinner than that of the tubular body 10. Because the tubular body 10 and the inflatable portion 11 are made of a set of the same materials, detachment of the inflatable portion 11 from the tubular body 10 can be prevented, and expansion of the tubular body 10 can also be prevented when a gas is supplied, allowing the inflatable portion 11 alone to be inflated. However, the material of the tubular body 10 may differ from that of the inflatable portion 11. Specific examples of the material include, but not limited to, silicon rubber, and synthetic resins such as polyolefine, polyamide, polyether polyamide, and polyurethane.

Figure 2A:
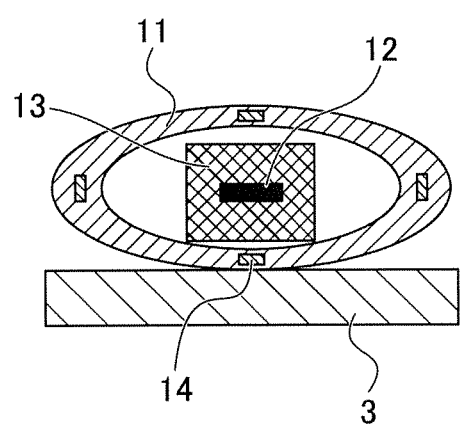
FIG. 2 shows a cross sectional view of an inflatable portion 11 of the biomagnetism measurement device 1 at the B—B' plane in FIG. 1.
Figure 2B:
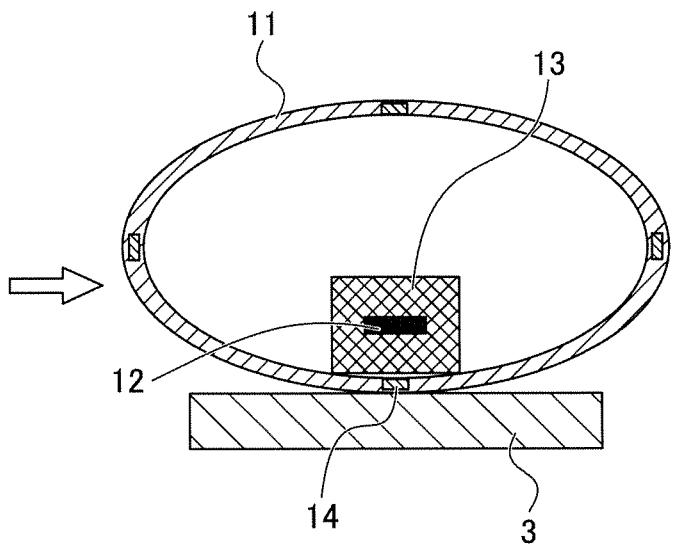

FIG. 2 is a cross sectional view of the inflatable portion 11 of the biomagnetism measurement device 1 at the B—B' plane in FIG. 1. FIG. 2(a) shows a state before the inflatable portion 11 is inflated with air, and FIG. 2(b) shows a state after the inflatable portion 11 is inflated with air. As shown in FIG. 1, the magnetic sensor portion 13 is fixed to the inner wall of the inflatable portion 11 of the biomagnetism measurement device 1 inserted into the esophagus 2. Consequently, the magnetic sensor part 13 is brought closer to the vertebra 3 when the inflatable portion 11 is inflated by supply of gas. This bring the position of the magnetic sensor portion 13 closer to a magnetic field source in the vertebra 3, allowing for more accurate measurement of magnetism.

Magnetic Sensor Portion 13

A magnetic field can be detected from outside the tubular body 10 with the magnetic sensor portion 13. The magnetic sensor portion 13 is fixed to the inner wall of the inflatable portion 11 in the biomagnetism measurement device 1 according to the embodiment 1 as described above. However, the magnetic sensor portion 13 may be configured in any fashion as long as the effects of the present invention can be obtained. Further, the magnetic sensor portion 13 preferably has a magnetic impedance element and/or a magnetic resistance element because the length of the outer long side in a tube cross-section of the tubular body 10 may become smaller.

Figure 3:
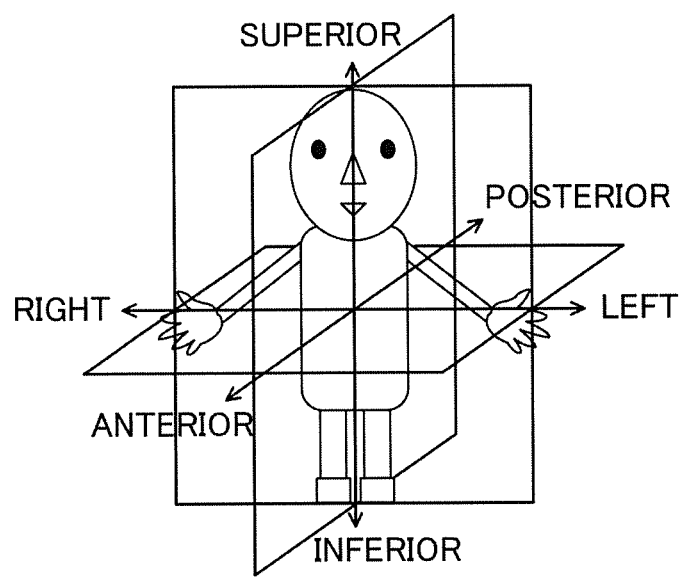
FIG. 3 shows directions in the anatomical position.

Further, the magnetic sensor portion 13 is preferably configured to allow for detection in an approximately constant direction so that a disordered area can be diagnosed more accurately. Further, it is preferably configured to allow for detection in an approximately constant direction in the anatomical position because a disordered area can be diagnosed even more accurately by understanding which direction in the body a magnetic field is detected from. In the embodiment 1, the magnetic sensor portion 13 was configured to allow for detection in an approximately constant direction in the anatomical position. There is no particular limitation for the approximately constant direction in the anatomical position, examples of which include the superior-inferior direction in the anatomical position, the right-left direction in the anatomical position, the anteroposterior direction in an anatomical position, and the like. Note that directions in the anatomical position as used herein are shown in FIG. 3.

There is no particular limitation for the lower limit of the number of the magnetic sensor portions 13, but it is preferably 2 or more, more preferably 3 or more, and even more preferably 4 or more because a disordered area can be accurately diagnosed. Further, there is no particular limitation for the upper limit of the number of the magnetic sensor portions 13, but it is preferably 10 or less, more preferably 8 or less, and even more preferably 6 or less because the area of the inflatable portion 11 can be minimized to reduce stress on the body.

When multiple magnetic sensor portions 13 are provided in the biomagnetism measurement device 1 according to the embodiment 1, at least one of the multiple magnetic sensor portions 13 is fixed to the inner wall, but there may be another magnetic sensor portion 13 which is not fixed to the inner wall. Note that a larger number of magnetic sensor portions 13 are preferably fixed to the inner wall because magnetism can be measured more accurately.

Connection Portion 12

Although not an essential component in the biomagnetism measurement device 1 according to the embodiment 1, the connection portion 12 may extend within the tube of the tubular body 10 in the approximately same direction as the longitudinal direction of the tubular body 10. The magnetic sensor portion 13 is fixed to the inner wall of the inflatable portion 11 in the biomagnetism measurement device 1 according to the embodiment 1 as described above. More specifically, the magnetic sensor portion 13 attached to the connection portion 12 at a desired position as shown in FIG. 1 is fixed to the inner wall of the inflatable portion 11. The connection portion 12 may be used to fix the magnetic sensor portion 13 at a desired position within the tube of the tubular body 10, but the magnetic sensor portion 13 is fixed to the inner wall of the inflatable portion 11 in the biomagnetism measurement device 1 according to the embodiment 1. Therefore, the connection portion 12 is optional, and may not be provided in the biomagnetism measurement device 1 according to the embodiment 1. Note that the term "desired position" in the connection portion 12 to which the magnetic sensor portion 13 of the biomagnetism measurement device 1 according to the embodiment 1 is attached refers to a position corresponding to a region in the inflatable portion 11 to which the magnetic sensor portion 13 is fixed.

Pressure Sensor 14

In the biomagnetism measurement device 1 according to the embodiment 1, a pressure sensor 14 is further provided inside the tubular body 10 as shown in FIG. 1. The pressure sensor 14 is a member for detecting the atmospheric pressure inside the inflatable portion 11. By virtue of the pressure sensor 14, a timing of stopping inflation can easily be determined. However, the pressure sensor 14 is optional, and may not be provided in the biomagnetism measurement device 1 according to the embodiment 1.

Any conventionally known pressure sensor can be used as the pressure sensor 14. For example, a piezoelectric element and the like can be used.

Method of Use

Below, an example of the method of using the biomagnetism measurement device 1 according to the embodiment 1 will be described.

Example of Use 1 Measurement a Magnetism from the Spine 4

Adjustment of the Position of a Magnetic Sensor

Figure 4:
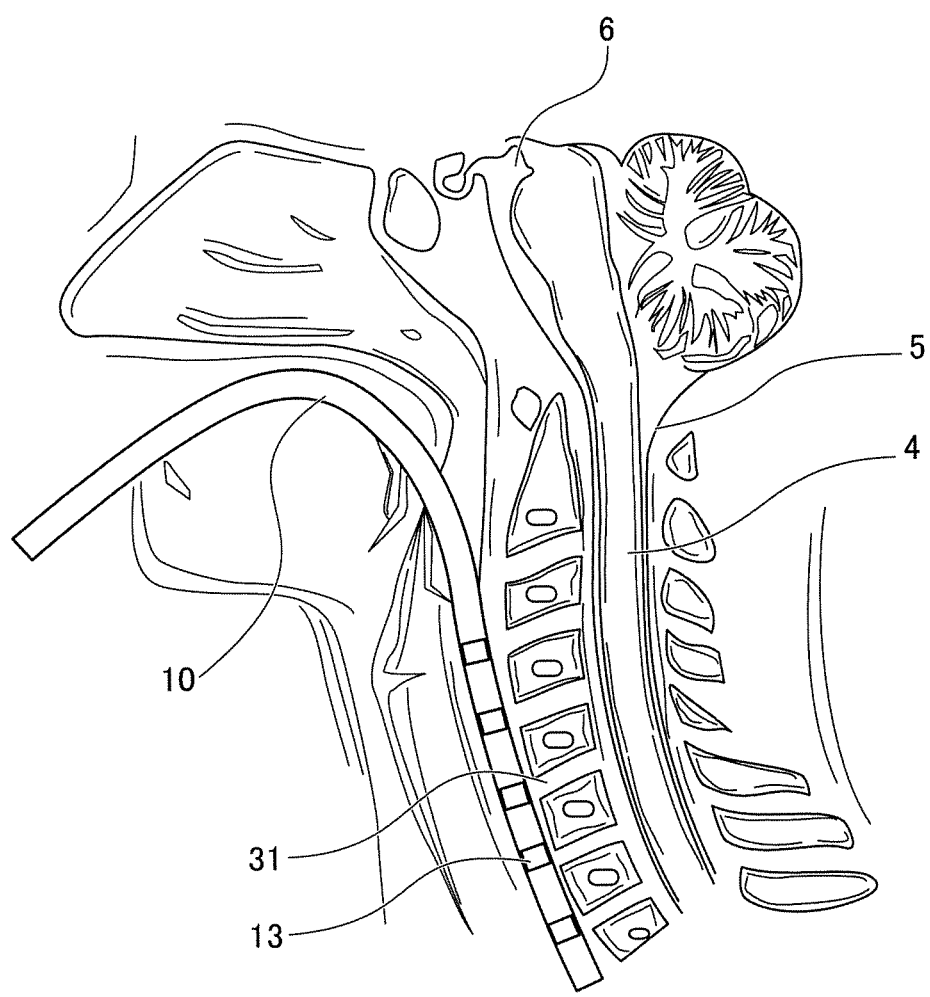
FIG. 4 shows a schematic view of the median sagittal cross section of a subject when the biomagnetism measurement device 1 according to the present invention is in use.

First, as shown in FIG. 4, the biomagnetism measurement device 1 is inserted through the mouth, the nose, or a blood vessel into a target position while monitoring the neck of a subject under radiography from the front or the side. Note that during this, signal output lines from the magnetic sensor portion 13 and the pressure sensor 14 are connected to an external signal processing unit (for example, a nerve-function monitor, an MEE-1200 series NEURO-MASTER: Nihon Kohden Corporation).

Adjustment of Inflation of the Inflatable Portion 11

When the biomagnetism measurement device 1 reaches the target position, the inflatable portion 11 is allowed to be inflated with air. During this, the degree of inflation of the inflatable portion 11 can be measured with the pressure sensor 14 provided in the biomagnetism measurement device 1, and the supply of air can be stopped when a predetermined pressure is reached (which can be appropriately selected depending on the size, wall thickness, and the like of the inflatable portion 11). Therefore, a timing of stopping inflation can easily be determined.

Setting-Up of a Stimulation Electrode

Subsequently, a stimulation electrode connected to an external stimulus-generating unit is fixed to the median nerve of the elbow. The stimulation electrode is set up so that for example, a pulse current of 0.3 to 4 mA is generated at 3 Hz.

Measurement of the Spine 4

When electrical stimuli from the elbow are moving up through the spine 4, a magnetic field is induced due to the electric current flowing through the spine 4. Each magnetic sensor can detect this induced magnetic field to output a signal as voltage. The output voltage from the sensor is transmitted to a signal processing unit through a signal output line. Stimulations by the stimulus electric power are repeated, for example, for 2000 times, and output voltage values from each magnetic sensor are arithmetically averaged for each stimulus treatment at the signal processing unit. Thereby, a magnetism from the spine 4 of a subject can be measured.

Example of Use 2 Measurement of a Magnetism from the Brain

In the biomagnetism measurement device 1 according to the present invention, the length of the outer long side of a tube cross-section of the tubular body 10 may be as short as 1 mm or less and the like so that the device can be allowed to pass through a blood vessel in the brain. A magnetism from the brain can be thus detected with the biomagnetism measurement device 1 according to the present invention which has passed through the brain. Thereby, functions in the deep brain which can not be measured through the body surface can be accurately diagnosed (for example, brain-death diagnosis and the like), and a cerebral function can also be diagnosed simply and conveniently. Below, a method of use will be described for the application.

Adjustment of the Position of a Magnetic Sensor

The biomagnetism measurement device 1 is inserted through a blood vessel into a target position in the brain while monitoring the brain of a subject under radiography. Note that during this, signal output lines from the magnetic sensor portion 13 and the pressure sensor 14 are connected to an external signal processing unit (for example, a nerve-function monitor, an MEE-1200 series NEURO-MASTER: Nihon Kohden Corporation) as in Example of Use 1.

Adjustment of Inflation of the Inflatable Portion 11

A similar method can be used as in Example of Use 1 as described above.

Measurement of a Magnetism Within the Brain

A magnetic field which may arise due to an electric current flowing inside the brain is measured, the electric current arising in response to a stimulus from an electrode punctured through the brain skin, the peripheral nerves stimulus of the limbs and the trunk, a transcranial magnetic stimulus, and the like. For example, the above stimulations are repeated for 300 times, and output voltage values from each magnetic sensor 13 are arithmetically averaged for each stimulus treatment at the signal processing unit. Thereby, a magnetism within the brain of a subject can be measured.

Example of Use 3 Measurement of a Magnetism from Heart Arrhythmia

The biomagnetism measurement device 1 according to the present invention can also be used to detect a magnetism from an arrhythmic site in the heart. Therefore, the arrhythmic site in the heart can be accurately diagnosed with the biomagnetism measurement device 1 according to the present invention. Further, heart arrhythmia can be diagnosed simply and conveniently with the biomagnetism measurement device 1 according to the present invention. Below, a method of use will be described for this application.

Adjustment of the Position of a Magnetic Sensor

The biomagnetism measurement device 1 is inserted through a blood vessel into a target position in the heart while monitoring the heart of a subject under radiography. Note that during this, signal output lines from the magnetic sensor portion 13 and the pressure sensor 14 are connected to an external signal processing unit (for example, a nerve-function monitor, an MEE-1200 series NEURO-MASTER: Nihon Kohden Corporation) as in Example of Use 1.

Adjustment of Inflation of the Inflatable Portion 11

A similar method can be used as in Example of Use 1 as described above.

Measurement of a Magnetism From Heart Arrhythmia

The magnetic sensor portion 13 is inserted to near the heart, and a magnetic field arising from an electric current flowing through the heart is measured to identify a magnetic field which may be responsible for arrhythmia. For example, an electrocardiogram is simultaneously measured along with magnetism, and arithmetic averaging of 300 values is performed to determine a waveform using R-wave progression as a trigger. Alternatively, a waveform of a magnetic field corresponding each heartbeat is directly determined without performing arithmetic averaging.

Example of Use 4 Measurement of a Magnetism from an Affected Area Using Magnetic Markers The biomagnetism measurement device 1 according to the present invention can also be used in combination with magnetic markers to measure a magnetism from the magnetic markers concentrated at an affected area. This allows a magnetism to arise from magnetic markers at an affected area which can be recognized with the magnetic markers (hereinafter, may also be referred to as an "affected area" in the present specification. Note that the affected area in FIG. 5 includes cancer cells). Therefore, the position of the affected area which is not visible from the body surface can be accurately diagnosed with the biomagnetism measurement device 1 according to the present invention. Further, the position of the affected area can be identified simply and conveniently.

Figure 5A:
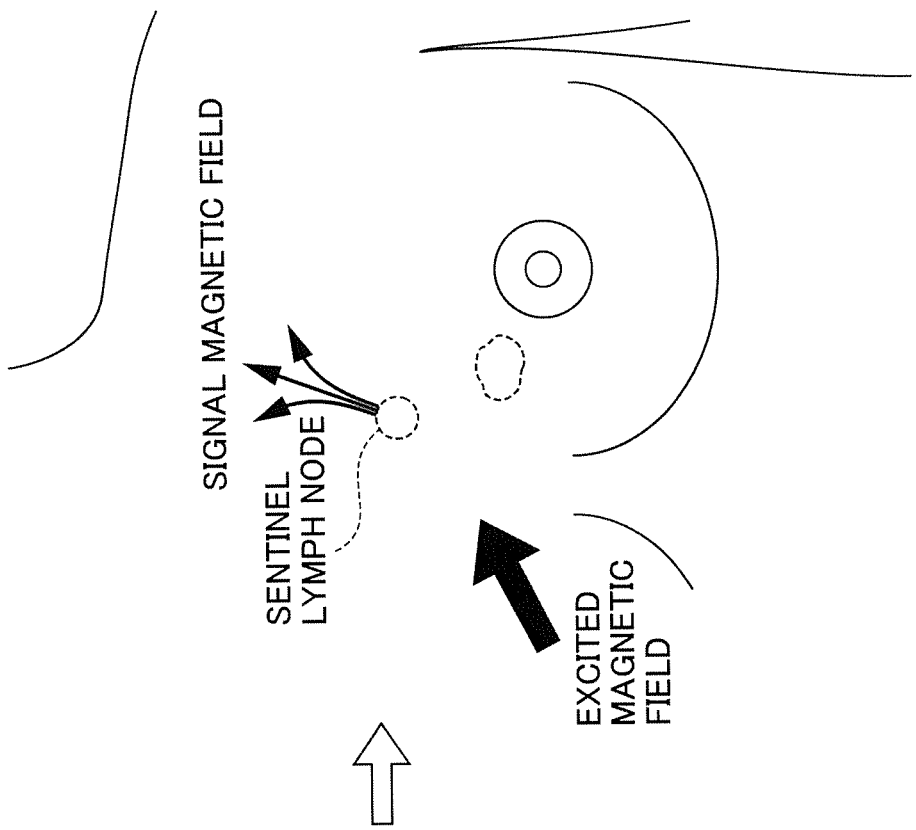
FIG. 5 shows an example of a procedure for detecting an affected area using magnetic markers and the biomagnetism measurement device according to the present invention.
Figure 5B:
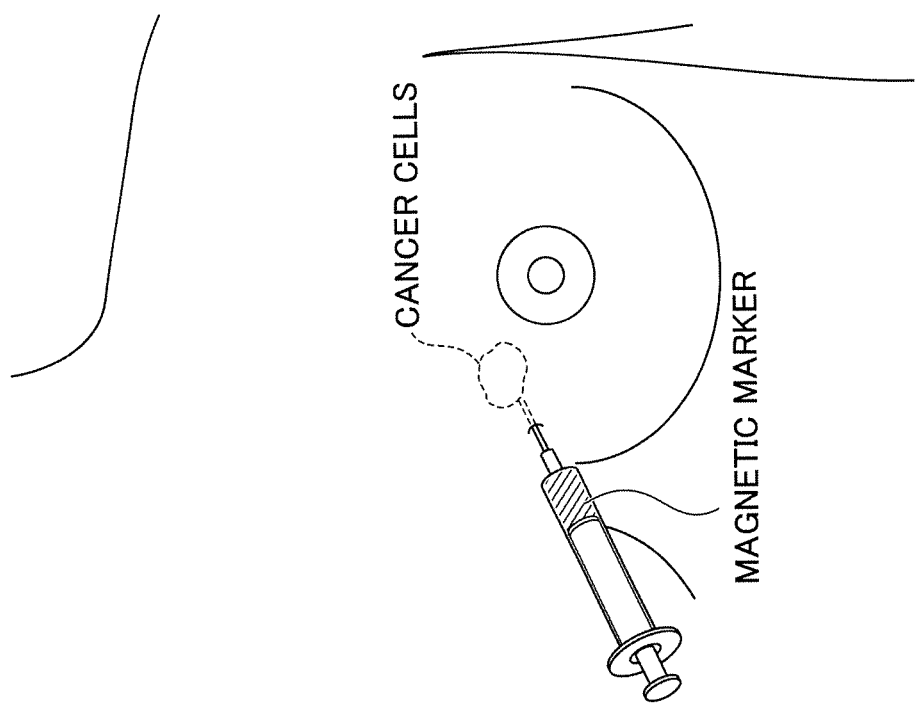

With reference to FIG. 5 as an example, as shown in FIG. 5(a), magnetic makers are injected through a blood vessel or directly into an affected area which can be recognized with the magnetic markers (hereinafter, may also be referred to as an "affected area" in the present specification. Note that the affected area in FIG. 5 includes cancer cells.) Then, the magnetic markers will reach the sentinel lymph node as the first lymph node via the lymph duct as shown in FIG. 5(b). If cancer cells have reached this lymph node, magnetic markers may bind with the affected area, and accumulate at the affected area. Thus, the position of the affected area which is not visible from the body surface can be detected by measuring magnetic signals from the magnetic markers accumulated at the lymph node using the biomagnetism measurement device 1 according to the present invention introduced into the body through a blood vessel and the like.

Further, with reference to FIG. 6 as an example, magnetic markers are injected through a blood vessel or directly into an affected area (the affected area in FIG. 6 includes cancer cells) to allow the magnetic markers to accumulate at the affected area as shown in FIG. 6(a). Under these conditions, the tubular body 10 of the biomagnetism measurement device 1 is inserted into the body of a subject to bring the magnetic sensor portion 13 closer to an affected area, and then an excitation magnetic field is generated with coils from the both sides of the body of the subject as shown in FIG. 6(b). This can allow detection of an affected area which is not visible from the body surface.

Below, a method of using the biomagnetism measurement device 1 according to the present invention in combination with magnetic markers will be described.

Adjustment of the Position of a Magnetic Sensor

Magnetic markers are injected through a blood vessel or directly into an affected area of a subject, and the biomagnetism measurement device 1 is inserted through the mouth, the nose, or a blood vessel into a target position (the affected area) while monitoring the stomach, intestinal tract, bladder, ureter, blood vessels and the like of the subject through an endoscope or under radiography. Note that during this, signal output lines from the magnetic sensor portion 13 and the pressure sensor 14 are connected to an external signal processing unit (for example, a nerve-function monitor, an MEE-1200 series NEURO-MASTER: Nihon Kohden Corporation) as in Example of Use 1.

Adjustment of Inflation of the Inflatable Portion 11

A similar method can be used as in Example of Use 1 as described above.

Measurement of a Magnetism from Magnetic Markers

An excitation magnetic field is applied from the outside of the body, and a magnetic field induced at the magnetic markers is then measured with a magnetic sensor present inside the body. Here, as an excitation magnetic field to be applied from the outside of the body, an alternating-current magnetic field or a combination of an alternating-current magnetic field and a direct-current magnetic field and the like can be used. A magnetic field from magnetic markers may increase or decrease depending on an applied magnetic field. This change can be detected with a magnetic sensor to identify a position where the magnetic markers are concentrated.

The biomagnetism measurement device 1 according to the embodiment 1 described above can provide the following effects.

The biomagnetism measurement device 1 was configured to include the tubular body 10; the inflatable portion 11 inflatable upon supply of gas, the inflatable portion 11 being located at a desired region of the tubular body 10; and the magnetic sensor portion 13 for detecting a magnetic field from outside the tubular body 10, the magnetic sensor portion 13 being fixed to an inner wall of the inflatable portion 11. Thereby, a disordered area (hereinafter, the term "disordered area" as used herein refers to a disordered area or affected area of the spine, brain, heart, and the like from which magnetism arises) can be accurately diagnosed with the biomagnetism measurement device 1 according to the present invention, and the biomagnetism measurement device 1 according to the present invention can be used simply and conveniently.

Further, the tubular body 10 and the inflatable portion 11 were configured to be made of the same material, and the wall thickness of the inflatable portion 11 was configured to be thinner than that of the tubular body 10. Because the tubular body 10 and the inflatable portion 11 are made of a set of the same materials in the biomagnetism measurement device 1 according to the present invention, detachment of the inflatable portion 11 from the tubular body 10 can be prevented, and expansion of the tubular body 10 can also be prevented when a gas is supplied, allowing the inflatable portion 11 alone to be inflated.

Further, the biomagnetism measurement device 1 was configured to further include the pressure sensor 14 for detecting the atmospheric pressure inside the inflatable portion 11. Thereby, a timing of stopping inflation can easily be determined for the biomagnetism measurement device 1 according to the present invention.

Further, the biomagnetism measurement device 1 was configured so that the magnetic sensor portion 13 was able to detect a magnetic field along an approximately constant direction in the anatomical position. This enables more accurate detection of a magnetic field, which in turn enables more accurate diagnosis of a disordered area.

Further, the biomagnetism measurement device 1 was configured so that the outer long side of a tube cross-section of the tubular body 10 was 5 mm or less, and the magnetic sensor portion 13 had a magnetic impedance element and/or a magnetic resistance element. This can further reduce the risk of damaging the spine 4, allowing for more convenient measurements of magnetism. Further, the biomagnetism measurement device 1 according to the present invention can be inserted into a blood vessel, the brain, and the like because the outer long side of a tube cross-section of the tubular body 10 is configured to be short as described above.

Further, the present invention can provide the biomagnetism measurement device 1 which can be used for detecting an affected area using magnetic markers. The conventional pathological examination for identifying an affected area requires a procedure of tissue examination under a microscope, which is time consuming and troublesome. According to the present invention, such a procedure can be avoided when using the biomagnetism measurement device 1 in combination of magnetic makers as described with reference to FIGS. 5 and 6, allowing for rapid and simple identification of the position of an affected area.

Embodiment 2

Below, the embodiment 2 will be described in detail with reference to FIGS. 7 to 9. For the configurations of the members with the same reference symbols as those used in the embodiment 1 above, differences from the embodiment 1 are mainly described, and repeated descriptions may be omitted.

Biomagnetism Measurement Device 1A

A biomagnetism measurement device 1A according to the embodiment 2 includes: a tubular body 10 having approximately elliptic inner shapes in tube cross-sections; at least one magnetic sensor portion 13 for detecting a magnetic field from outside the tubular body 10; and a connection portion 12 extending within the tube of the tubular body 10 in the approximately same direction as the longitudinal direction of the tubular body 10, and having the at least one magnetic sensor portion 13 attached at a desired position, in which the length L2 of an inner short side of at least one cross section among the tube cross-sections is shorter than the length L1 of the connection portion 12 in the direction of an inner long side of the same cross section as the at least one cross section, and the length L3 of the inner long side of the at least one cross section is longer than the length L1 of the connection portion 12 in the direction of the inner long side of the same cross section. FIG. 7 shows a schematic cross sectional view of the biomagnetism measurement device 1A according to the embodiment 2, and also shows schematically an aspect of use thereof. FIG. 8 shows a cross sectional view of the tubular body 10 of the biomagnetism measurement device 1A at the A-A' plane in FIG. 7. FIG. 9 shows a cross sectional view of the inflatable portion 11 of the biomagnetism measurement device 1A at the B—B' plane. Below, each of the components of the biomagnetism measurement device 1A according to the embodiment 2 will be described.

Tubular Body 10

As shown in FIG. 8, the tubular body 10 of the biomagnetism measurement device 1A according to the embodiment 2 has approximately elliptic inner shapes in tube cross-sections.

The length L2 of the inner short side of at least one cross section among the tube cross-sections of the tubular body 10 is shorter than the length L1 of the connection portion 12 in the direction of the inner long side of the same cross section as the at least one cross section, and the length L3 of the inner long side of the at least one cross section is longer than the length L1 of the connection portion 12 in the direction of the inner long side of the same cross section. In FIG. 8, FIG. 8(a) shows a state before the tubular body 10 is inflated with air, and FIG. 8(b) shows a state after the tubular body 10 is inflated with air. As shown in FIGS. 8(a) and 8(b), the inflatable portion 11 is inflated (see FIG. 9 as described below) while the tubular body 10 is not when air is put into the tubular body 10. Therefore, the connection portion 12 will not be twisted within the tubular body 10 even upon inflation. This enables accurate detection of a magnetic field, which in turn enables more accurate diagnosis of a disordered area. Further, expansion of the tubular body 10 can be partly prevented when configured as described above, reducing restriction in a blood flow when the tubular body 10 is inserted into a blood vessel.

Further, the length L2 of the inner short side is short than the length L1 of the connection portion 12, and the length L3 of the inner long side is longer than the length L1 of the connection portion 12 for preferably at least one cross section, preferably for two or more cross sections, more preferably for three or more cross sections, and even more preferably for four or more cross sections in view that a magnetic field can be detected more accurately.

There is no particular limitation for the length of the outer long side of a tube cross-section of the tubular body 10 for the biomagnetism measurement device 1A according to the embodiment 2 as in the biomagnetism measurement device 1 according to the embodiment 1, but it is preferably 5 mm or less, more preferably 4 mm or less, and even more preferably 3 mm or less.

Further, there is no particular limitation for the outer shape of a tube cross-section, but it is preferred to be an approximately elliptic shape because the tube itself will be resistant to twisting within the esophagus 2.

Inflatable Portion 11

Figure 7:
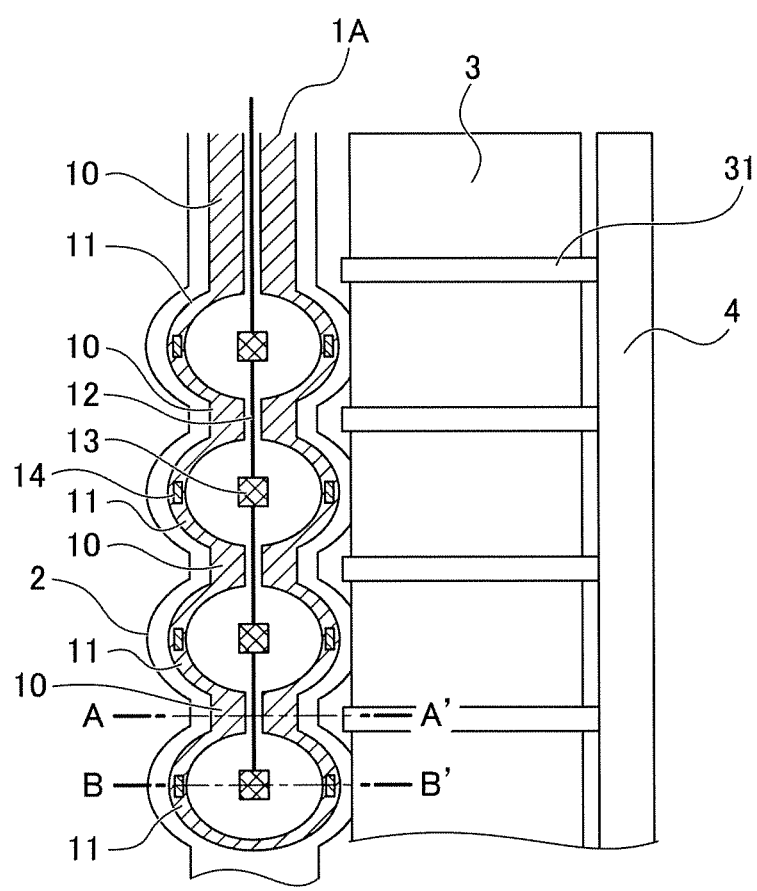
FIG. 7 shows a schematic cross sectional view of a biomagnetism measurement device 1A according to the embodiment 2 of the present invention, and also shows schematically an aspect of use thereof.

As shown in FIG. 7, the biomagnetism measurement device 1A according to the embodiment 2 includes at least one inflatable portion 11. The at least one inflatable portion 11 is located at a desired region of the tubular body 10, and can be inflated by supply of gas. However, the biomagnetism measurement device 1A according to the embodiment 2 may be configured without the at least one inflatable portion 11.

When the biomagnetism measurement device 1A according to the embodiment 2 includes the at least one inflatable portion 11, the at least one inflatable portion 11 includes multiple inflatable portions 11, and the at least one magnetic sensor portion 13 includes multiple magnetic sensor portions 13 to prevent twisting of the entire connection portion 12, and consequently to prevent twisting of the at least one magnetic sensor portion 13. Preferably, the multiple magnetic sensor portions 13 are individually accommodated inside each of the multiple inflatable portions 11. This configuration allows noninflatable portions and the inflatable portions 11 to be arranged alternately in the longitudinal direction of the tubular body 10, reliably preventing twisting of the connection portion 12 in the noninflatable portions. This in turn can prevent twisting of the magnetic sensor portions 13. This enables accurate detection of a magnetic field, which in turn enables more accurate diagnosis of a disordered area.

Figure 9A:
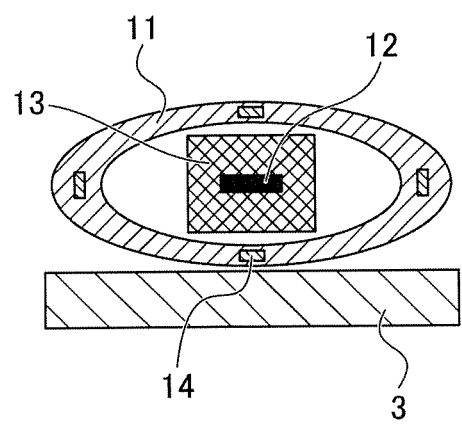
FIG. 9 shows a cross sectional view of the inflatable portion 11 of the biomagnetism measurement device 1A at the B—B' plane in FIG. 7.
Figure 9B:
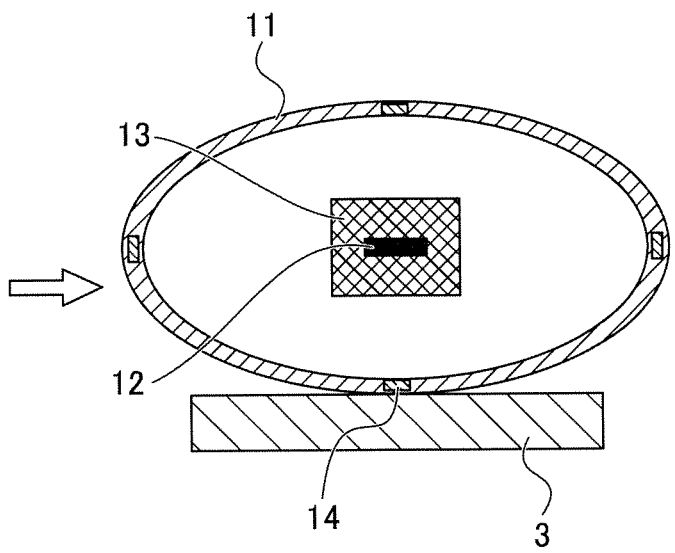

There is no particular limitation for the "desired region of the tubular body 10" in the biomagnetism measurement device 1 according to the embodiment 2, but it is preferably a region where the noninflatable portions (portions other than the inflatable portions 11 of the tubular body 10) and the inflatable portions 11 are arranged alternately in the longitudinal direction of the tubular body 10 as shown in FIG. 7. FIG. 9 shows a cross sectional view of the inflatable portion 11 of the biomagnetism measurement device 1A at the B—B' plane. FIG. 9(a) shows a state before the inflatable portion 11 is inflated with air, and FIG. 9(b) shows a state after the inflatable portion 11 is inflated with air. As shown in FIG. 9(b), the inflatable portion 11 is inflated when air is put into the tubular body 10. This can prevent twisting of the tubular body itself within the esophagus 2.

There is no particular limitation for the materials and the wall thicknesses of the tubular body 10 and the inflatable portions 11, but the tubular body 10 and the inflatable portions 11 are preferably made of the same material, and the wall thicknesses of the inflatable portions 11 are preferably thinner than the wall thickness of the tubular body 10 as in the biomagnetism measurement device 1 according to the embodiment 1.

Connection Portion 12

The connection portion 12 extends within the tube of the tubular body 10 in the approximately same direction as the longitudinal direction of the tubular body 10, and has the magnetic sensor portions 13 attached at desired positions. Note that in the biomagnetism measurement device 1A according to the embodiment 2, there is no particular limitation for the "desired positions" in the connection portion 12 to which the magnetic sensor portions 13 are attached, and they can be any positions as long as a magnetic field can be detected there. However, they are preferably positions corresponding to the inflatable portions 11 as shown in FIG. 7 when the inflatable portions 11 are provided.

Magnetic Sensor Portion 13

The magnetic sensor portions 13 are attached to desired positions of the connection portion 12 in the biomagnetism measurement device 1A according to the embodiment 2 as described above. For the biomagnetism measurement device 1A according to the embodiment 2, preferably, the magnetic sensor portions 13 each have a magnetic impedance element and/or a magnetic resistance element as in the biomagnetism measurement device 1 according to the embodiment 1. Further, the magnetic sensor portions 13 are preferably configured so that detection in an approximately constant direction can be achieved in order to detect biomagnetism more accurately. Further, they are preferably configured to allow for detection in an approximately constant direction in the anatomical position because a disordered area can be diagnosed even more accurately by understanding which direction in the body a magnetic field is detected from. There is no particular limitation for the approximately constant direction, and it may be any direction.

Further, the biomagnetism measurement device 1A according to the embodiment 2 includes the pressure sensor 14 as in the biomagnetism measurement device 1 according to the embodiment 1, but the pressure sensor 14 is optional and may not be provided.

Method of Use

The biomagnetism measurement device 1A according to the embodiment 2 can be used by similar ways as the biomagnetism device according to the embodiment 1.

The biomagnetism measurement device 1A according to the embodiment 2 described above can provide the following effects.

The biomagnetism measurement device 1A according to the embodiment 2 includes: a tubular body 10 having approximately elliptic inner shapes in tube cross-sections; at least one magnetic sensor portion 13 for detecting a magnetic field from outside the tubular body 10; and a connection portion 12 extending within a tube of the tubular body 10 in the approximately same direction as the longitudinal direction of the tubular body 10, and having the at least one magnetic sensor portion 13 attached at a desired position, in which the length L2 of an inner short side of at least one cross section among the tube cross-sections is shorter than the length L1 of the connection portion 12 in the direction of an inner long side of the same cross section as the at least one cross section, and the length L3 of the inner long side of the at least one cross section is longer than the length L1 of the connection portion 12 in the direction of the inner long side of the same cross section. Thereby, a disordered area can be accurately diagnosed with the biomagnetism measurement device 1 according to the present invention, and the biomagnetism measurement device 1 according to the present invention can be used simply and conveniently.

Embodiment 3

Below, the embodiment 3 will be described in detail with reference to FIG. 10. For the configurations of the members with the same reference symbols as those used in the embodiment 1 above, differences from the embodiment 1 are mainly described, and repeated descriptions may be omitted.

The biomagnetism measurement device 1B according to the embodiment 3 includes a magnetic sensor portion 13A for detecting a magnetic field along the approximately superior-inferior direction in the anatomical position, the magnetic sensor portion 13A being provided at a desired position within the tube of the tubular body 10. FIG. 10 is a schematic sectional view of the biomagnetism measurement device 1B according to the embodiment 3, and also shows schematically an aspect of use thereof. Below, each of the components of the biomagnetism measurement device 1B according to the embodiment 3 will be described.

Tubular Body 10

Figure 10:
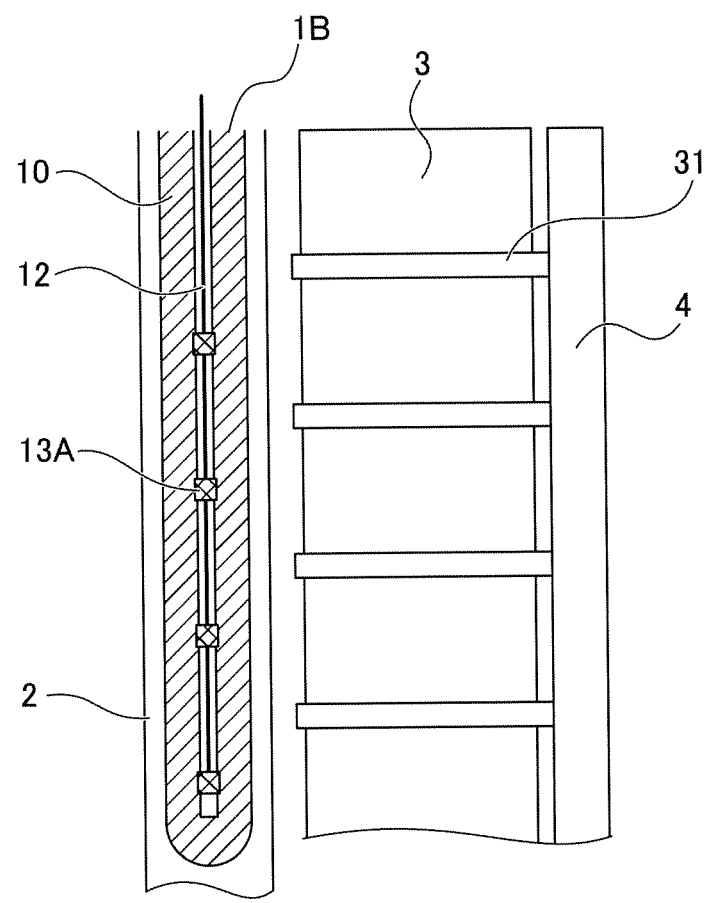
FIG. 10 shows a schematic cross sectional view of a biomagnetism measurement device 1B according to the embodiment 3 of the present invention, and also shows schematically an aspect of use thereof.

As shown in FIG. 10, in the tubular body 10 of the biomagnetism measurement device 1B according to the embodiment 3, the magnetic sensor portion 13A is provided at a desired position. There is no particular limitation for the "desired position within the tube of the tubular body 10" in the biomagnetism measurement device 1B according to the embodiment 3, and it may be any position where a magnetic field can be detected.

There is no particular limitation for the length of the outer long side of a tube cross-section of the tubular body 10 as in the biomagnetism measurement device 1 according to the embodiment 1, but it is preferably 5 mm or less, more preferably 4 mm or less, and even more preferably 3 mm or less. Further, there is no particularly limitation for the cross sectional shapes (inner shape, outer shape) of the tubular body 10, but they may be elliptic or circular. However, the outer shape of a cross section is preferred to be approximately elliptic because the tube itself will be resistant to twisting within the esophagus 2.

Magnetic Sensor Portion 13A

The magnetic sensor portion 13A is provided at a desired position within the tube of the tubular body 10 in the biomagnetism measurement device 1B according to the embodiment 3 as described above. Further, the tubular body 10 of the biomagnetism measurement device 1B according to the embodiment 3 can detect a magnetic field along the approximately superior-inferior direction in the anatomical position. This allows accurate measurement of magnetism even if the magnetic sensor portion 13A is twisted.

Connection Portion 12

As shown in FIG. 10, the biomagnetism measurement device 1B according to the embodiment 3 includes the connection portion 12 extending within the tube of the tubular body 10 in the approximately same direction as the longitudinal direction of the tubular body 10 and having the magnetic sensor portion 13A attached to a desired position. However, the connection portion 12 may not necessarily be provided in the biomagnetism measurement device 1B according to the embodiment 3. The connection portion 12 may not be provided when the magnetic sensor portion 13 can be fixed within the tube, for example, such as by being fixed to the inner wall of the tubular body 10. Note that there is no particular limitation for the "desired position" to which the magnetic sensor portion 13A is attached in the biomagnetism measurement device 1B according to the embodiment 3, and it may be any position where a magnetic field can be detected.

The biomagnetism measurement device 1B according to the embodiment 3 does not include the inflatable portion 11 and the pressure sensor 14. However, it may be configured to include the inflatable portion 11 and the pressure sensor 14.

Method of Use

Methods of using the biomagnetism measurement device 1B according to the embodiment 3 are similar to those for the biomagnetism measurement device 1 according to the embodiment 1 except that a step of "adjusting inflation of the inflatable portion 11" in the biomagnetism measurement device 1 according to the embodiment 1 is not included because the biomagnetism measurement device 1B according to the embodiment 3 does not have the inflatable portion 11.

The biomagnetism measurement device 1B according to the embodiment 3 described above can provide the following effects.

The biomagnetism measurement device 1B according to the embodiment 3 was configured to include the magnetic sensor portion 13A for detecting a magnetic field along the approximately superior-inferior direction in the anatomical position, the magnetic sensor portion 13A being provided at a desired position within the tube of the tubular body 10. Thereby, a disordered area can be accurately diagnosed with the biomagnetism measurement device 1 according to the present invention even when the magnetic sensor portion 13A is twisted, and the biomagnetism measurement device 1 according to the present invention can be used simply and conveniently.

Embodiment 4

Below, the embodiment 4 will be described in detail with reference to FIGS. 11 to 13. For the configurations of the members with the same reference symbols as those used in the embodiment 1 above, differences from the embodiment 1 are mainly described, and repeated descriptions may be omitted. Note that the biomagnetism measurement device 10 according to the embodiment 4 is configured by altering the configuration of the magnetic sensor portion 13 in the biomagnetism measurement device 1 according to the embodiment 1.

The biomagnetism measurement device 10 according to the embodiment 4 includes: a tubular body 10; and an inflatable portion 11 inflatable by supply of gas, the inflatable portion 11 being positioned at a desired position of the tubular body 10; multiple magnetic sensor portions 13 for detecting a magnetic field from outside the tubular body 10, the multiple magnetic sensor portions 13 being fixed to the inner wall of the inflatable portion 11, in which at least one of the multiple magnetic sensor portions 13 includes a triaxial magnetic sensor for detecting magnetic fields along three mutually orthogonal axes, or includes multiple magnetic sensors closely arranged and capable of detecting magnetic fields along three mutually orthogonal axes, and the rest of the multiple magnetic sensor portions 13 each include a uniaxial magnetic sensor for detecting a magnetic field along one predetermined axis among the three axes. FIG. 11 shows a schematic cross sectional view of the biomagnetism measurement device 10 according to the embodiment 4, and also shows schematically an aspect of use thereof. Below, each of the components of the biomagnetism measurement device 10 according to the embodiment 4 will be described.

Tubular Body 10

The biomagnetism measurement device 10 according to the embodiment 4 includes the inflatable portion 11 positioned at a desired region as in the biomagnetism measurement device 1 according to the embodiment 1. Further, it includes the pressure sensor 14 within the tubular body 10 as in the biomagnetism measurement device 1 according to the embodiment 1.

Further, there is no particular limitation for the length of the outer long side of a tube cross-section of the tubular body 10, but it is preferably 5 mm or less, more preferably 4 mm or less, and even more preferably 3 mm or less as in the biomagnetism measurement device 1 according to the embodiment 1. Further, there is no particularly limitation for the cross sectional shapes (inner shape, outer shape) of the tubular body 10, but they may be elliptic or circular. However, the outer shape of a cross section is preferred to be approximately elliptic because the tube itself will be resistant to twisting within the esophagus 2.

Inflatable Portion 11

The inflatable portion 11 is positioned at a desired region of the tubular body 10. Further, in the biomagnetism measurement device 10 according to the embodiment 4, the magnetic sensor portions 13 are fixed to the inner wall of the inflatable portion 11 as in the biomagnetism measurement device 1 according to the embodiment 1. This can prevent twisting of the magnetic sensor portions 13 within the tubular body 10 in the biomagnetism measurement device 10 according to the embodiment 4, leading to accurate diagnosis of a disordered area. Note that there is no particular limitation for the "desired region of the tubular body 10" in the biomagnetism measurement device 10 according to the embodiment 4 as long as it is a region where the effects of the present invention can be obtained, but it may be, for example, a region in the end side of the tubular body 10 as shown in FIG. 11, or alternatively, it may be a region other than the end of the tubular body 10.

Moreover, there is no particular limitation for the materials and the wall thicknesses of the tubular body 10 and the inflatable portion 11, but the tubular body 10 and the inflatable portion 11 are preferably made of the same material, and the wall thickness of the inflatable portion 11 is preferably thinner than that of the tubular body 10 as in the biomagnetism measurement device 1 according to the embodiment 1.

Magnetic Sensor Portion 13

The biomagnetism measurement device 1C according to the embodiment 4 has the multiple magnetic sensor portions 13. The magnetic sensor portions 13 can be configured in any way as long as the effects of the present invention can be obtained, but the magnetic sensor portions 13 in the biomagnetism measurement device 1C according to the embodiment 4 are fixed to the inner wall of the inflatable portion 11 as in the biomagnetism measurement device 1 according to the embodiment 1.

In the biomagnetism measurement device 1C according to the embodiment 4, at least one of the multiple magnetic sensor portions 13 includes a triaxial magnetic sensor for detecting magnetic fields along three mutually orthogonal axes, or includes multiple magnetic sensors closely arranged and capable of detecting magnetic fields along three mutually orthogonal axes. The directions of the three axes may or may not be related to the directions in the anatomical position. When the at least one of the magnetic sensor portions 13 is configured as described above, the position of the sensor can be identified while reading a magnetic field from a magnetic field source attached on the outside of the body, leading to more accurate diagnosis of a disordered area. Further, the aforementioned directions of the three axes are preferably related to the directions in the anatomical position because a disordered area can be diagnosed even more accurately by understanding which direction in the body a magnetic field is detected from.

The magnetic sensor portions 13 other than the above magnetic sensor are uniaxial magnetic sensors for each detecting a magnetic field along one predetermined axis among the three axes. There is no particular limitation for the magnetic field along one predetermined axis, and it may be in any direction.

Figure 11:
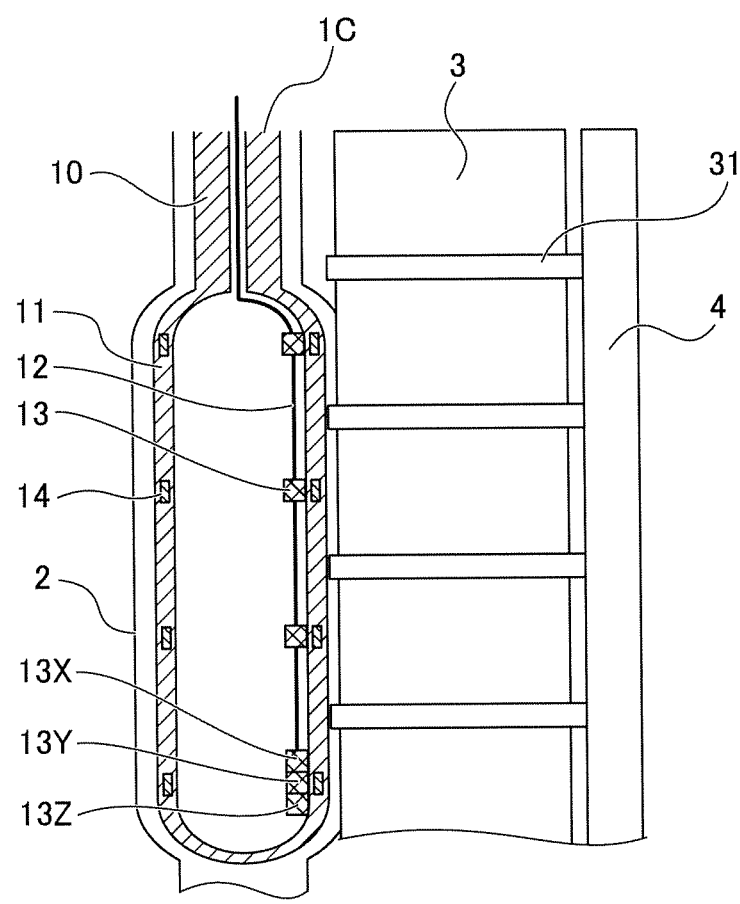
FIG. 11 shows a schematic cross sectional view of a biomagnetism measurement device 10 according to the embodiment 4 of the present invention, and also shows schematically an aspect of use thereof.

FIG. 11 shows an embodiment in which one of the multiple magnetic sensor portions 13 includes 3 magnetic sensors; magnetic sensors 13X, 13Y, and 13Z, the magnetic sensors 13X, 13Y, and 13Z being closely arranged. The magnetic sensor 13X can detect a magnetic field along an axis orthogonal to the axes of magnetic fields which can be detected with the magnetic sensors 13Y and 13Z. The magnetic sensor 13Y can detect a magnetic field along an axis orthogonal to the axes of magnetic fields which can be detected with the magnetic sensors 13X and 13Z. The magnetic sensor 13Z can detect a magnetic field along an axis orthogonal to the axes of magnetic fields which can be determined with the magnetic sensors 13X and 13Y. In FIG. 11, shown is a configuration in which one of the multiple magnetic sensor portions 13 includes 3 magnetic sensors (13X, 13Y, 13Z). However, the configuration is not limited to this. Two or more magnetic sensor portions 13 may each include 3 magnetic sensors. Alternatively, a triaxial magnetic sensor may be used instead of the three magnetic sensors, or a triaxial magnetic sensor may be used in combination of the three magnetic sensors.

Further, the magnetic sensor portions 13 preferably have a magnetic impedance element and/or a magnetic resistance element, which may allow a shorter length of the outer long side of a tube cross-section of the tubular body 10, as in the biomagnetism measurement device 1 according to the embodiment 1.

Connection Portion 12

The connection portion 12 extends within the tube of the tubular body 10 in the approximately same direction as the longitudinal direction of the tubular body 10. The magnetic sensor portions 13 are fixed to the inner wall of the inflatable portion 11 in the biomagnetism measurement device 10 according to the embodiment 4 as described above. More specifically, the magnetic sensor portions 13 attached to the connection portion 12 at desired positions are fixed to the inner wall of the inflatable portion 11 as shown in FIG. 11. The connection portion 12 is used to fix the magnetic sensor portions 13 at desired positions within the tube of the tubular body 10, but the magnetic sensor portions 13 are fixed to the inner wall of the inflatable portion 11 in the biomagnetism measurement device 10 according to the embodiment 4. Therefore the connection portion 12 is optional, and may not be provided in the biomagnetism measurement device 10 according to the embodiment 4. Note that the "desired positions" in the connection portion 12 of the biomagnetism measurement device 10 according to the embodiment 4 to which the magnetic sensor portions 13 are attached are positions corresponding to the regions in the inflatable portion 11 to which the magnetic sensor portions 13 are attached.

Pressure Sensor 14

The biomagnetism measurement device 10 according to the embodiment 4 further includes the pressure sensor 14 as in the biomagnetism measurement device 1 according to the embodiment 1.

Method of Use

Methods of using the biomagnetism measurement device 10 according to the embodiment 4 are similar to those for the biomagnetism measurement device 1 according to the embodiment 1 except for the step of adjusting the position of a magnetic sensor. In the biomagnetism measurement device 10 according to the embodiment 4, adjustment of the position of a magnetic sensor can be performed according to the following procedures.

Figure 12:
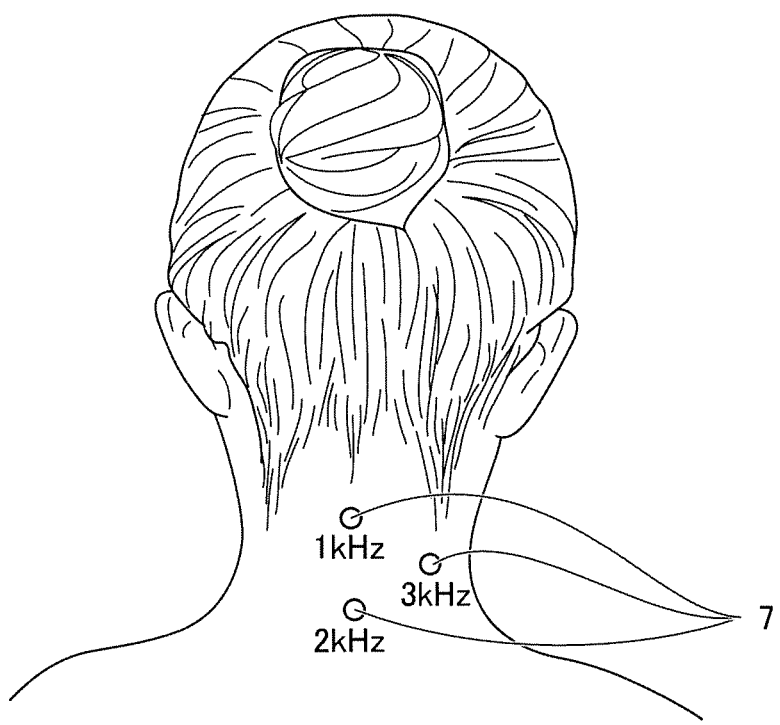
FIG. 12 shows magnetic field sources on a subject for use with the biomagnetism measurement device 1C according to the present invention.
Figure 13:
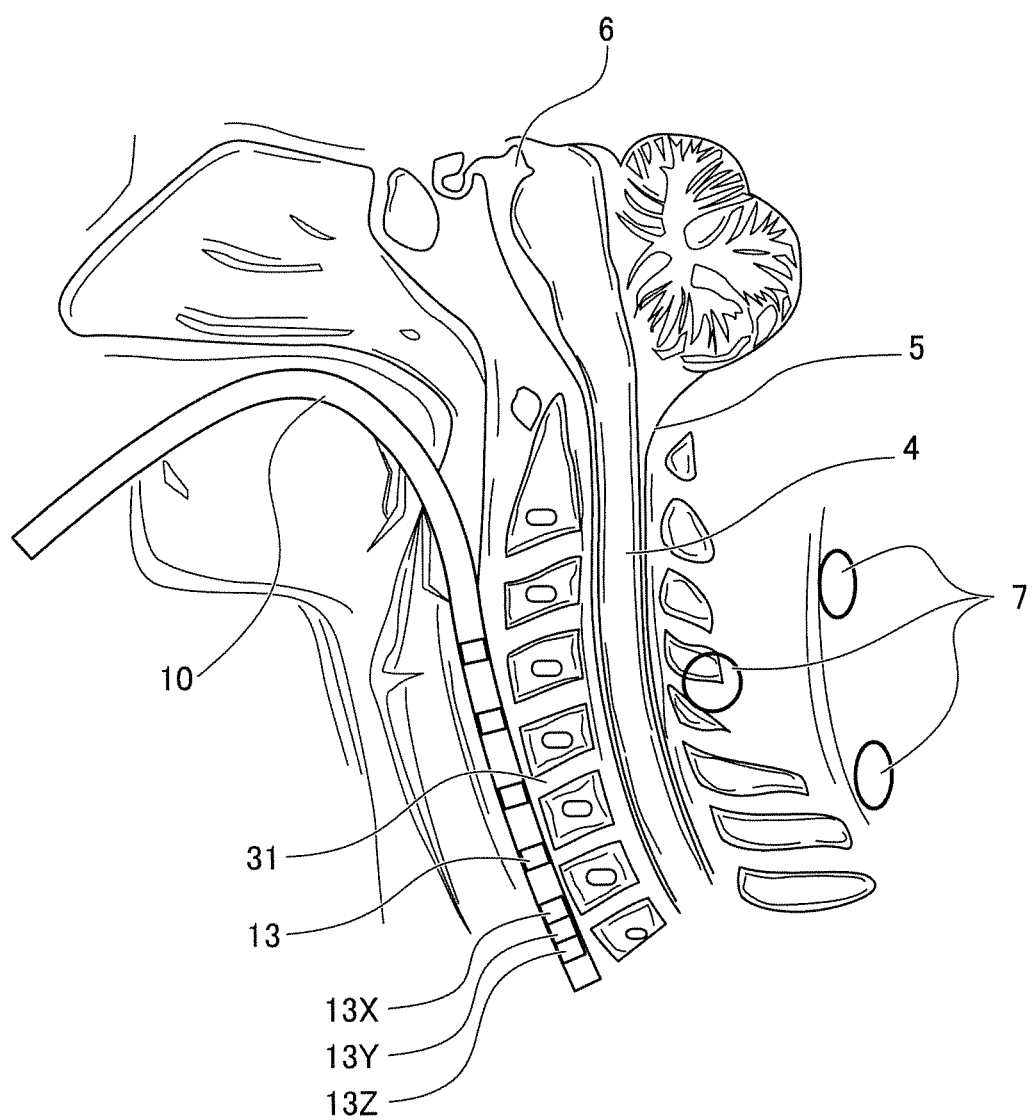
FIG. 13 shows a schematic view of the median sagittal cross section of a subject when the biomagnetism measurement device 1C according to the present invention is in use.

As shown in FIG. 12, sources of magnetism serving as the references for determining the position of the magnetic sensor portion 13 are attached at three locations around the neck of a subject. The three sources of magnetism are each allowed to generate different frequencies (for example, 1 kHz, 2 kHz, 3 kHz). Subsequently, the positional relationship between the cervical spine and the magnetic field sources is determined by radiography of the neck of the subject from the front or the side. As shown in FIG. 13, the tubular body 10 of the biomagnetism measurement device 10 which has been magnetized is inserted through the mouth or the nose into the esophagus 2, then into a target position. Then, magnetic fields from the magnetic field sources are detected with the magnetic sensors 13X, 13Y, and 13Z or a triaxial magnetic sensor. Thereby, how far the sensors enter can be determined.

Note that the step of adjusting inflation of the inflatable portion 11 is omitted when the biomagnetism measurement device 10 according to the embodiment 4 is configured without having the inflatable portion 11.

The biomagnetism measurement device 10 according to the embodiment 4 described above can provide the following effects.

The biomagnetism measurement device 10 according to the embodiment 4 was configured to include the multiple magnetic sensor portions 13 so that at least one of the multiple magnetic sensor portions 13 includes a triaxial magnetic sensor for detecting magnetic fields along three mutually orthogonal axes, or includes multiple magnetic sensors closely arranged and capable of detecting magnetic fields along three mutually orthogonal axes, and the other magnetic sensor portions 13 includes a uniaxial magnetic sensor for detecting a magnetic field along one predetermined axis among the three axes. Thereby, the position of a sensor can be identified while reading a magnetic field from a magnetic field source attached on the outside of the body, leading to more accurate diagnosis of a disordered area.

Embodiment 5

Below, the embodiment 5 will be described in detail with reference to FIG. 14. For the configurations of the members with the same reference symbols as those used in the embodiment 4 above, differences from the embodiment 4 are mainly described, and repeated descriptions may be omitted.

The biomagnetism measurement device 1D according to the embodiment 5 includes a tubular body 10 and at least one or more magnetic sensor portions 13 provided at desired positions of the tubular body 10, in which each of the at least one or more magnetic sensor portions 13 includes a triaxial magnetic sensor for detecting magnetic fields along three mutually orthogonal axes, or includes multiple magnetic sensors closely arranged and capable of detecting magnetic fields along three mutually orthogonal axes. FIG. 14 shows a schematic cross sectional view of the biomagnetism measurement device 1D according to the embodiment 5, and also shows schematically an aspect of use thereof. Below, each of the components of the biomagnetism measurement device 1D according to the embodiment 5 will be described.

Tubular Body 10

Figure 14:
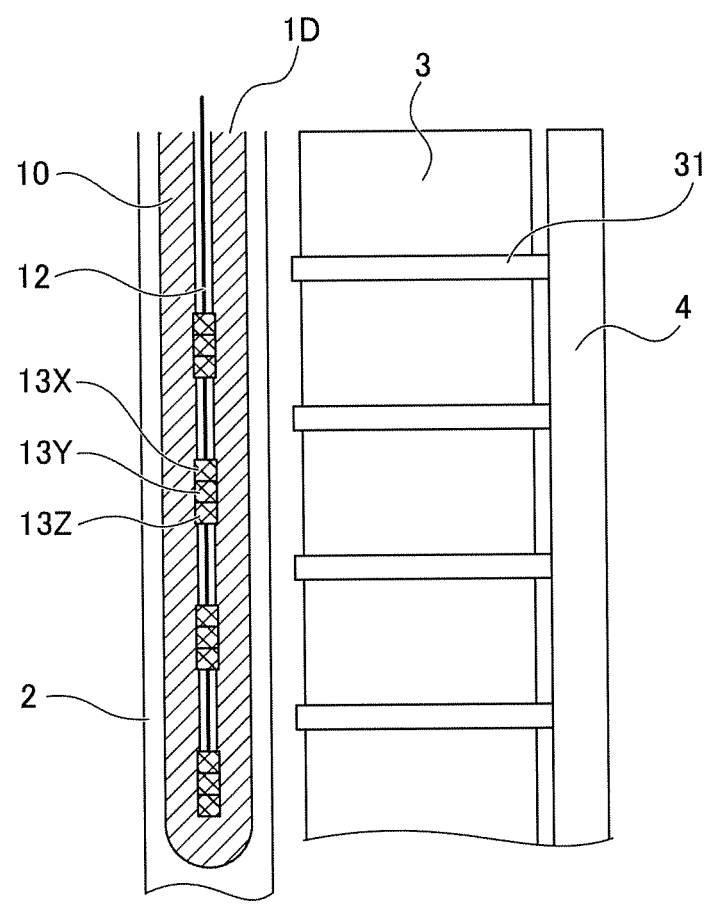
FIG. 14 shows a schematic cross sectional view of a biomagnetism measurement device 1D according to the embodiment 5 of the present invention, and also shows schematically an aspect of use thereof.

As shown in FIG. 14, the tubular body 10 of the biomagnetism measurement device 1D according to the embodiment 5 includes a magnetic sensor portion 13A provided at a desired position. There is no particular limitation for the "desired position within the tube of the tubular body 10" in the biomagnetism measurement device 1D according to the embodiment 5, and it may be any position where a magnetic field can be detected.

There is no particular limitation for the length of the outer long side of a tube cross-section of the tubular body 10, but it is preferably 5 mm or less, more preferably 4 mm or less, and even more preferably 3 mm or less as in the biomagnetism measurement device 1 according to the embodiment 1. Further, there is no particularly limitation for the cross sectional shapes (inner shape, outer shape) of the tubular body 10, but they may be elliptic or circular. However, the outer shape of a cross section is preferred to be approximately elliptic because the tube itself will be resistant to twisting within the esophagus 2.

Magnetic Sensor Portion 13

The biomagnetism measurement device 1D according to the embodiment 5 includes at least one or more magnetic sensor portions 13 provided at desired positions of the tubular body 10, in which each of the at least one or more magnetic sensor portions 13 includes a triaxial magnetic sensor for detecting magnetic fields along three mutually orthogonal axes, or includes multiple magnetic sensors closely arranged and capable of detecting magnetic fields along three mutually orthogonal axes. Each of the at least one or more magnetic sensor portions 13 is triaxial as described above, allowing for determination of the orientation thereof. Therefore, a disordered area can be accurately diagnosed even when the magnetic sensor portions 13 are twisted. Further, the directions of the above three axes may or may not be related to the directions in the anatomical position, but a configuration in which an approximately constant direction can be detected is preferred. Further, the directions of the above three axes are preferably related to the directions in the anatomical position because a disordered area can be diagnosed even more accurately by understanding which direction in the body a magnetic field is detected from.

FIG. 14 shows an embodiment in which each of the at least one or more magnetic sensor portions 13 includes three magnetic sensors: magnetic sensors 13X, 13Y, and 13Z, the magnetic sensors 13X, 13Y, and 13Z being closely arranged. However, the configuration is not limited this. A triaxial magnetic sensor may be used instead of the three magnetic sensors (13X, 13Y, 13Z), or a triaxial magnetic sensor may be used in combination of the three magnetic sensors.

There is no particular limitation for the lower limit of the number of the magnetic sensor portions 13, but it is preferably 2 or more, more preferably 3 or more, and even more preferably 4 or more because a disordered area can be accurately diagnosed. Further, there is no particular limitation for the upper limit of the number of the magnetic sensor portions 13, but it may be, for example, 10 or less, 9 or less, 8 or less, 7 or less, 6 or less, and the like.

The magnetic sensor portions 13 may be provided at desired positions in any manner as long as the effects of the present invention can be obtained, but they are provided at desired positions of the tubular body 10 by being attached at desired positions of the connection portion 12 in the case of the biomagnetism measurement device 1D according to the embodiment 5.

Connection Portion 12

The biomagnetism measurement device 1D according to the embodiment 5 further includes the connection portion 12. All of the multiple magnetic sensor portions 13 are attached at desired positions of the connection portion 12. These desired positions can be anywhere as long as the effect of the present invention can be obtained. However, it is merely required that all of the multiple magnetic sensor portions 13 are provided at desired positions of the tubular body 10. Therefore, the biomagnetism measurement device 1D according to the embodiment 5 does not necessarily need to include the connection portion 12, for example, when the multiple magnetic sensor portions 13 are directly fixed to the inner wall of the tubular body 10.

The biomagnetism measurement device 1D according to the embodiment 5 does not include the inflatable portion 11 and the pressure sensor 14. However, it may be configured to include the inflatable portion 11 and the pressure sensor 14.

Method of Use

Methods of using the biomagnetism measurement device 1D according to the embodiment 5 are similar to those for the biomagnetism measurement device 1C according to the embodiment 4 except that the following step is performed after the step of adjusting the position of a magnetic sensor. Specifically, for the biomagnetism measurement device 1D according to the embodiment 5, the following step is performed after the step of adjusting the position of a magnetic sensor.

The magnetic sensors 13X, 13Y, and 13Z or a triaxial magnetic sensor are used to detect corresponding magnetic fields from the three magnetic field sources. The direction from which a magnetic field along each axis is detected is determined from the intensity detected in each of the three axes.

Note that the step of adjusting inflation of the inflatable portion 11 is omitted.

The biomagnetism measurement device 1D according to the embodiment 5 described above can provide the following effects.

The biomagnetism measurement device 1D according to the embodiment 5 was configured to include a tubular body 10; multiple magnetic sensor portions 13 provided at desired positions of the tubular body 10, in which each of the multiple magnetic sensor portions 13 includes a triaxial magnetic sensor for detecting magnetic fields along three mutually orthogonal axes, or includes multiple magnetic sensor portions 13 closely arranged and capable of detecting magnetic fields along three mutually orthogonal axes. Thereby, a disordered area can be accurately diagnosed even when the magnetic sensor portions 13 are twisted, and the device can be used simply and conveniently.

Variations

The biomagnetism measurement device according to the embodiments 1 to 5 of the present invention are described hereinbefore. The present invention, however, shall not be limited to the aforementioned embodiments 1 to 5, and modifications may be made approximately.

For example, when the multiple magnetic sensor portions 13 are provided in the embodiment 2, some of the multiple magnetic sensor portions 13 may be fixed to the inner wall as in the embodiment 1.

Further, the biomagnetism measurement device 10 according to the embodiment 4 as described above corresponds to the biomagnetism measurement device 1 according to the embodiment 1 in which the configuration of the magnetic sensor portion 13 is altered. However, it may be configured such that the configuration of the magnetic sensor portion 13 in the biomagnetism measurement device 1B according to the embodiment 2 is altered so as to be capable of detecting magnetic fields along three axes. That is, the biomagnetism measurement device 10 according to the embodiment 4 may be configured to include the multiple magnetic sensor portions 13 of the biomagnetism measurement device 1B according to the embodiment 2, in which at least one of the multiple magnetic sensor portions 13 includes a triaxial magnetic sensor for detecting magnetic fields along three mutually orthogonal axes, or includes multiple magnetic sensors closely arranged and capable of detecting magnetic fields along three mutually orthogonal axes. Alternatively, the biomagnetism measurement device 1B according, to the embodiment 3 may be configured to include the aforementioned triaxial sensor portion 13 in addition to the magnetic sensor portion 13A.

Further, the above embodiments 1 to 5 may be configured to include a functionality for sending and receiving a signal to/from the outside in the connection portion 12. However, a device for sending and receiving a signal to/from the outside may not necessarily be provided in the connection portion 12, but may be provided anywhere in a biomagnetism measurement device so that a signal can be sent or received to/from the outside. For example, a wireless communication functionality may be implemented in each of the magnetic sensor portions 13 to send and receive a signal to/from the outside.

Further, the tubular body 10 may be configured to be flexible so that the tubular body 10 can flexibly follow a blood vessel when inserted through the blood vessel and the like. This enables easy insertion of the tubular body 10 into a blood vessel and the like. Therefore, the tubular body 10 is preferably configured to be flexible. In order to configure the tubular body 10 to be flexible, the conventionally known methods, for example, those used for a catheter having a flexible tip can be used. More specifically, the tubular body 10 may be configured such that for example, a manipulation disk (dial) with a rotation functionality is attached to the tubular body 10 at the distal side, the disk having two wires attached thereto, and the two wires extend through the tube and are fixed to the front end of the tubular body 10. Thereby, the direction of the front end of the tubular body 10 can be changed by operating the dial at the distal side.

Further, the aforementioned embodiments 1, 2, and 4 are each configured to include the pressure sensor 14, but the configuration is not limited to this. The pressure sensor 14 may not be provided. Moreover, pressure may be measured with a different means, instead of using the pressure sensor 14 provided at the inflatable portion 11. Examples of such a means include, for example, a means including an expansion device with a pressure gage at the entrance of the tube. The pressure inside the inflatable portion 11 can be determined by measuring the pressure inside the expandable portion (a portion to be pressurized for expansion) of the expansion device.

EXPLANATION OF REFERENCE NUMERALS

1 Biomagnetism measurement device according to Embodiment 1
1A Biomagnetism measurement device according to Embodiment 2
1B Biomagnetism measurement device according to Embodiment 3
1C Biomagnetism measurement device according to Embodiment 4
1D Biomagnetism measurement device according to Embodiment 5
10 Tubular body
11 Inflatable portion
12 Connection portion
13 Magnetic sensor portion
13A Magnetic sensor portion for detecting a magnetic field along the superior-inferior direction in the anatomical position
13X Magnetic sensor for detecting a magnetic field along an axis orthogonal to the axes of magnetic fields which can be detected with the magnetic sensors 13Y and 13Z
13Y Magnetic sensor for detecting a magnetic field along an axis orthogonal to the axes of magnetic fields which can be detected with the magnetic sensors 13X and 13Z
13Z Magnetic sensor for detecting a magnetic field along an axis orthogonal to the axes of magnetic fields which can be detected with the magnetic sensors 13X and 13Y
14 Pressure sensor
2 Esophagus
3 Vertebra
31 Intervertebral disc
4 Spine
5 Dura mater
6 Basilar artery
7 Magnetic field source
L1 Length of a connection portion in the direction of the inner long side of the same cross section as the tube cross-section
L2 Inner short side of the tube cross-section
L3 Long and short sides of the tube cross-section

The invention claimed is:

1. A biomagnetism measurement device, comprising:
a tubular body having approximately elliptic inner shapes in perpendicular tube cross-sections, wherein the approximately elliptic inner shapes have a first length of a first inner side and a second length of a second inner side such that the first length is less than the second length; and
a magnetic sensor portion for detecting a magnetic field from outside the tubular body,
wherein the tubular body is free of an inflatable portion, has approximately elliptic outer shapes in perpendicular tube cross-sections, the elliptic outer shapes having an outer long side that is 5 mm or less, and has an inner wall at a distal side thereof, the inner wall having a space between the inner wall and the magnetic sensor portion, and
wherein the magnetic sensor portion is configured to detect a magnetic field along an approximately constant direction in an anatomical position.

2. The biomagnetism measurement device according to claim 1, wherein the magnetic sensor portion comprises multiple magnetic sensor portions, and
at least one of the multiple magnetic sensor portions comprises a triaxial magnetic sensor for detecting magnetic fields along three mutually orthogonal axes, or comprises multiple magnetic sensors closely arranged and capable of detecting magnetic fields along three mutually orthogonal axes, and
all others of the multiple magnetic sensor portions each comprise a uniaxial magnetic sensor for detecting a magnetic field along one predetermined axis among the three axes.

3. The biomagnetism measurement device according to claim 1, wherein
the magnetic sensor portion has a magnetic impedance element and/or a magnetic resistance element.

4. The biomagnetism measurement device according to claim 1, further comprising:
an inflatable portion inflatable upon supply of gas, the inflatable portion being located at a required region of the tubular body,
wherein the magnetic sensor portion is fixed to an inner wall of the inflatable portion.

5. The biomagnetism measurement device according to claim 4, wherein the tubular body and the inflatable portion comprise the same material, and
the wall thickness of the inflatable portion is thinner than that of the tubular body.

6. The biomagnetism measurement device according to claim 1, further comprising:
a connection portion extending within a tube of the tubular body in an approximately same direction as a longitudinal direction of the tubular body, having approximately elliptic shapes in cross-sections, and having the magnetic sensor portion attached at a desired position.

\* \* \* \* \*